United States Patent [19]

Pollner

[11] 4,152,234
[45] May 1, 1979

[54] SOLID CLOSED ENDED TUBULAR OXYGEN SENSOR

[75] Inventor: Rudolf Pollner, Bamberg, Fed. Rep. of Germany

[73] Assignee: Robert Bosch GmbH, Stuttgart, Fed. Rep. of Germany

[21] Appl. No.: 868,627

[22] Filed: Jan. 11, 1978

[30] Foreign Application Priority Data

Jan. 11, 1977 [DE] Fed. Rep. of Germany ....... 2700807

[51] Int. Cl.² .......................................... G01N 27/58
[52] U.S. Cl. ................................................ 204/195 S
[58] Field of Search ............... 204/1 S, 195 S; 324/29

[56] References Cited

U.S. PATENT DOCUMENTS 3,723,279  3/1973  Fruehan et al. .................. 204/195 S
3,776,831  12/1973  Roy et al. .......................... 204/195 S
3,791,954  2/1974  Makoto et al. .................... 204/195 S Primary Examiner—G. L. Kaplan
Attorney, Agent, or Firm—Frishauf, Holtz, Goodman & Woodward

[57] ABSTRACT

A solid closed ended tubular oxygen sensor element, particularly useful for sensing the oxygen content of exhaust gases from internal combustion engines. The closed end of the tubular element which is adapted to be exposed to the hot exhaust gases is made of zirconium oxide stabilized with yttrium oxide and/or ytterbium dioxide. The remaining main portion of the tubular element is made of zirconium dioxide stabilized with calcium oxide. The invention also provides methods of manufacturing these tubular elements.

9 Claims, 6 Drawing Figures

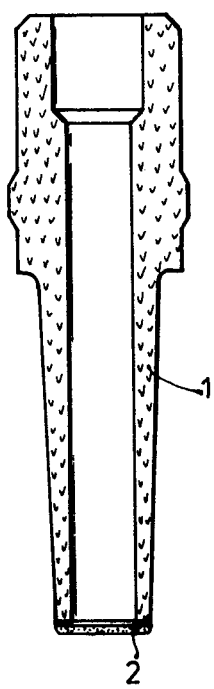
Fig.1
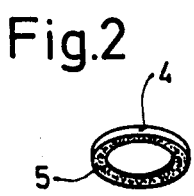
Fig.2
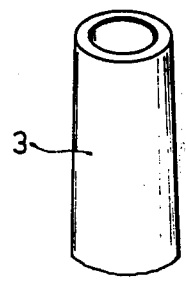
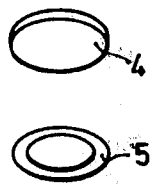
Fig.3
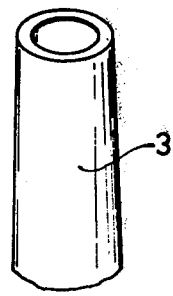

SOLID CLOSED ENDED TUBULAR OXYGEN SENSOR

Cross reference to related United States Patent Applications which are assigned to the assignee of the present application: U.S. Pat. Nos. 3,841,987; 3,891,529; 3,960,692; 3,960,693; 3,978,006; 4,019,974; 4,021,326.

BACKGROUND OF THE INVENTION

Tubular elements having a closed end and composed of a solid electrolyte for use in the determination of the oxygen content in gases, particularly exhaust gases from internal combustion engines, are known (see, for example, said US Pat. No. 4,021,326). These known elements which consist of zirconium dioxide stabilized with calcium oxide have the inherent disadvantage of only being operative at above 500° C.

It is also known to stabilize zirconium dioxide with yttrium oxide, or ytterbium oxide, or with a mixture of both of these oxides. A so-called yttrium concentrate which in addition to yttrium oxide contains oxides of the heavy rare earth metals, can also be used in place of yttrium oxide as an additive to stabilize zirconium dioxide.

Zirconium dioxide which has been stabilized with yttrium oxide or ytterbium oxide when compared with zirconium dioxide stabilized with calcium oxide, is characterized by an increase of electrical conductivity in the range of one order of magnitude and exhibits a greater degree of ionization. Because of these beneficial characteristics, sensors made from such solid electrolytes are operative at temperatures of approximately 350° C. and higher. Sensors prepared from zirconium dioxide stabilized with ytterbium dioxide have a threshold temperature which is even somewhat lower than said approximately said 350° C.

Technically, it is possible to produce a tubular solid electrolyte element made of zirconium dioxide stabilized with yttrium oxide and/or ytterbium oxide. Because of the high cost of yttrium oxide and the even higher cost of ytterbium oxide when compared with calcium oxide, it is prohibitive economically to produce a zirconium oxide solid electrolyte stabilized with yttrium oxide and/or ytterbium oxide.

Based on a consideration of cost factors, an attempt has been made to join an end plate made of zirconium dioxide stabilized with yttrium oxide to the end of a metal tube. However, because of the difference in physical properties of these two components at the high working temperatures, difficulties arose in connection with the joining and sealing of the yttrium oxide stabilized zirconium dioxide and the metal.

THE INVENTION

The present invention provides a tubular sensor element for the determination of the oxygen content of gases, usually the exhaust gases from an internal combustion engine, comprising a solid electrolyte tubular element having a closed end. The closed end portion of the solid electrolyte consists essentially of zirconium dioxide stabilized with yttrium oxide and/or ytterbium oxide. The remaining portion of the solid electrolyte comprises zirconium dioxide stabilized with calcium oxide. The closed end portion of the said sensor element consisting essentially of zirconium dioxides stabilized with yttrium oxide and/or ytterbium oxide is preferably in the form of a thin plate end portion or a rounded, for example, spherical, end portion. The end portion consisting essentially of zirconium dioxide stabilized with yttrium oxide and/or ytterbium oxide preferably contains between about 4 and 15 mole percent yttrium oxide and/or ytterbium oxide. The zirconium dioxide stabilized with calcium oxide preferably contains between about 8% and 25 mole percent of calcium oxide. These stabilized zirconium dioxides may also contain additives which are beneficial in the sintering process.

The solid sensor tube closed by a flat plate may be prepared by compressing (briquetting) a mixture consisting essentially of zirconium dioxide stabilized with yttrium oxide and/or ytterbium oxide, which may optionally be annealed, to form the plate which has not been sintered. This plate is joined to the flat face of a calcium oxide stabilized zirconium tube by a ceramic slip containing zirconium dioxide stabilized with calcium oxide and/or yttrium oxide and/or ytterbium oxide. The excessive ceramic slip is removed by grinding and smoothing the area of joinder prior to the final sintering operation.

The tubular element having a flat end plate may also be manufactured by first sintering the thin plate of zirconium dioxide which has been stabilized with yttrium oxide and/or ytterbium oxide to form a sintered plate which is then fused to the flat end of the sintered calcium oxide stabilized zirconium dioxide tube using molten glass for the joining operation. This joinder may be carried out by applying an aqueous suspension of glass powder or a suspension of glass powder in an organic medium using a spraying, immersing, paint application, or pressing technique in the form of an annular ring on one surface of the sintered thin plate. The glass powder may contain adjuvants to assist in the binding operation. The glass may also be applied by positioning a ring comprising powdered glass in an organic binder between the flat face of the sintered tube and the thin end plate. In each case, a solid unit is formed by heating the assembly of the open tube, the intermediate glass composition or ring, and the sintered thin plate until the glass melts and fuses the assembly together.

The tubular element having the rounded end is preferably formed in a pressing operation as set forth in detail hereinafter.

BRIEF DESCRIPTION OF THE DRAWINGS:

FIG. 1 is a cross-section of the tubular sensor element having a thin plate closing one end.

FIGS. 2 and 3 are exploded perspective views illustrating two different methods of joining the end plate to the tubular portion of the element.

In FIG. 1, the solid sensor includes the tubular portion 1 composed of a calcium oxide stabilized zirconium oxide ceramic mass closed at one end with a thin plate 2 composed of a zirconium dioxide stabilized with yttrium oxide or ytterbium oxide ceramic material. The closed end is the one adapted to be exposed to the exhaust gases. The embodiment of the invention disclosed in FIG. 1 may be manufactured by a number of methods with those discussed hereinafter being preferred.

Figure 4:
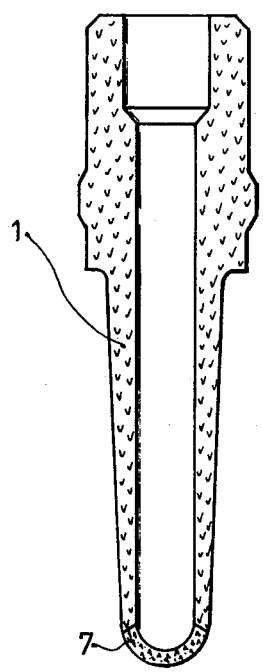
FIG. 4 is a cross-sectional view of the tubular sensor element with one end closed by a rounded end member.

A preformed green tubular element of zirconium dioxide stabilized with calcium oxide is joined to a green thin plate of similar dimensions composed of zirconium dioxide stabilized with, for example, yttrium oxide. The aforenoted preformed green members may be merely in the as formed state, for example, briquetted or pressed, or they may be annealed. A slip made of zirconium dioxide stabilized with calcium oxide or yttrium oxide in an aqueous suspension is applied to a flat end face of the tubular element. The thin plate is pressed squarely onto this end face. After drying and removal of the excess dried slip by grinding, the assembly is sintered at about 1600° C. to form an integral unit in which the thin end plate is fixed to the tube. The amount of shrinkage of the two ceramics utilized must be closely matched to avoid fracture at the sintered area of joinder. By way of example, such a closed end tubular element may be prepared wherein the end plate ceramic is a zirconium dioxide stabilized with 8 mole percent of yttrium oxide which is produced from a mixture of 86.3% by weight of powdered monoclinic zirconium dioxide having a specific surface of about 5 m$^2$/g and 13% by weight of yttrium oxide. This mixture is then pulverized to a powder having a specific surface value (BET) of at least 8 m$^2$/g. The calcium oxide stabilized zirconium dioxide consists essentially of 99.5% by weight of zirconium dioxide which is stabilized with 15 mole percent of calcium oxide (presintered at 1300° C.) and which contains 0.5% by weight of kaolin. This ceramic is also pulverized to a specific surface (BET) of at least 8 m$^2$/g.

The sensor element illustrated in FIG. 1 may also be prepared from components which have already been sintered rather than using green or annealed components. As shown in FIG. 2, a layer 5 composed of powdered glass in an organic binder is applied as an annular ring on one surface of the end plate 4 composed of the yttrium oxide and/or ytterbium oxide stabilized zirconium dioxide. The end plate 4 with the glass annulus 5 applied thereto is then contacted with the corresponding flat end portion of the tubular calcium oxide stabilized zirconium dioxide element 3. They are then heated, for example, at 1200–1250° C. to melt the glass and fuse the elements 4 and 3 together. Upon cooling, a strong assembly is obtained. The powdered glass of ring 5 should have a coefficient of expansion identical or very close to that of the sintered ceramic elements. The glass should also have a softening point sufficiently high that the element remains stable at the operating service temperatures during the life of the oxygen sensor.

FIG. 3 illustrates a similar method in which an annulus 5 made of powdered glass containing an organic binder which is prepared by, for example, pressing, rolling, or stamping, is positioned between the tubular element 3 and the end plate 4 to form an assembly which is then heated at the elevated temperature to fuse and form the integral closed end tubular element as described in connection with the embodiment of FIG. 2.

The sensor of FIG. 4 also comprises a calcium oxide stabilized zirconium dioxide tube 1 with the closed end which is adapted to be exposed to gases for sensing the oxygen content thereof closed with a small rounded element 7 made of the yttrium oxide and or ytterbium oxide stabilized zirconium dioxide.

The tubular sensor having a rounded closed end as disclosed in FIG. 4 is produced by a quasi-isostatic pressure method wherein the pressure is applied through a rubber casing to form the green compact which is subsequently ground or otherwise machined into the final shape. Pressure methods using either the rubberbag method or the rubber-tube method can be used. The rubber-tube method is illustrated in the processes described with reference to FIGS. 5 and 6.

The lower end of the press form (rubber form) 8 is closed by means of plug 9 which bears the centrally located press mandrel 10. A mass 11 of zirconium oxide stabilized with calcium oxide, preferably a granulated mixture, is filled into the space between the casing 8 and the mandrel 10 up to the level indicated by the line 12. Zirconium dioxide stabilized with yttrium oxide and/or ytterbium oxide 13 is then placed above the ceramic mass 11 until the upper portion of the space is filled. Solid plug 14 is then placed above the ceramic 13 to seal the rubber-encased apparatus which is then subjected to hydraulic pressure applied radially to produce a pressure-formed green body having the shape illustrated by the dashed line 15. After pressure release, the mandrel 10 is withdrawn from the encased body when the mold is open. The pressure-formed green compact having the outer shape indicated by the dashed line 15 is then ground into a shape having the outer surface indicated by the dotted line 16. This shaped pressed green body is then sintered in the known manner for sintering zirconium dioxide at about 1600° C. The respective compositions of the tubular element portion and the end portion can be the same as that set forth hereinbefore in connection with the formation of the flat-ended tube using preformed pressed green materials and sintering them after they have been joined in the green compact form, i.e., zirconium dioxide stabilized with 8 mole percent yttrium oxide; and zirconium dioxide stabilized with calcium oxide comprising 99.5% by weight of zirconium dioxide and 15 mole percent calcium oxide with 0.5% by weight of kaolin. The masses discussed in connection with this method are powdery mixtures having the characteristics set forth hereinbefore.

In order to minimize the possibility of fracture at the area of joinder of the rounded end portion and the tubular end portion, the physical characteristics and particularly the heat shrinkage during sintering and the coefficient of expansion of the sintered materials must be closely matched for said two ceramic components.

Figure 5:
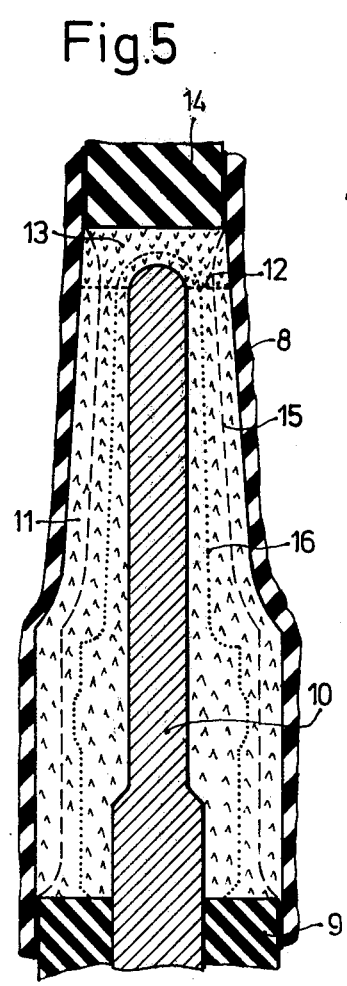
FIGS. 5 and 6 are cross-sectional views through a casing illustrating two different methods of manufacturing the element illustrated in FIG. 4.
Figure 6:
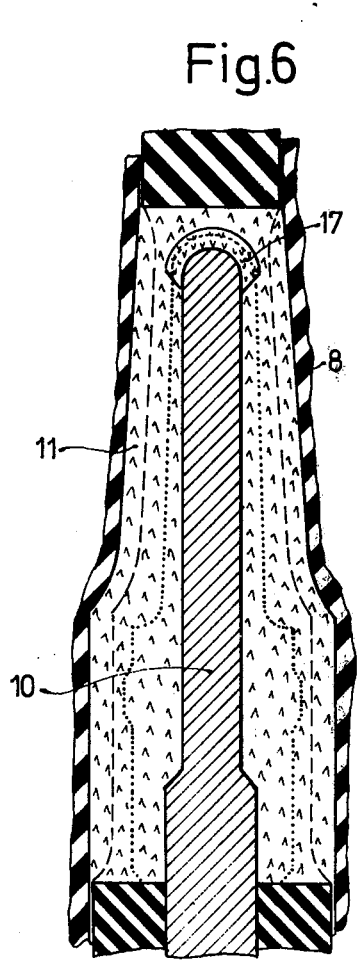

FIG. 6 illustrates a cross-section of another embodiment of the method using pressure applied through a rubber form as described hereinbefore. A preformed rounded end piece 17 shaped to correspond to the end of the mandrel which is made of zirconium dioxide stabilized with yttrium oxide and/or ytterbium dioxide is located at the end of the mandrel 10 which is centrally located in the rubber casing 8 having one end closed with plug 9. The space in the casing is then completely filled with a powdery mass 11 of calcium oxide stabilized zirconium dioxide. The remaining steps of the process are the same as those described hereinbefore in connection with the embodiment using the apparatus illustrated in FIG. 5.

The completed closed end tubular sensor, as is well known, contains inner and outer electrodes (usually catalytic) and preferably a porous ceramic coating over the outer electrode. These electrodes may be platinum layers. The inner platinum contact and also the outer catalytic electron conductive electrode, usually also platinum containing, can be applied on the respective inner and outer surfaces of the sintered zirconium dioxide solid electrolyte by deposition from the vapor state, metal sputtering, flame spraying, thick film technology, etc. The catalytic electron conductive layer (preferably platinum containing) on the outer surface of the solid electrolyte preferably covers the end portion of the tube which is prepared from the zirconium dioxide stabilized with yttrium oxide and/or ytterbium oxide and is preferably limited to that portion of the tube. This catalytic electrode covering the end of the tube is electrically connected to the upper portion of the tube by an axially extending conductive strip which extends up over the flange portion of the tubular element onto the upper flat rim at the open end of the tubular element and is adapted to make contact with an electric contact element. The outer electrode coating is preferably coated with a porous coating of magnesium spinel which may be applied by known means, for example, by plasma spraying. Other coatings may be applied directly or sequentially on the solid electrolyte, for example, as described in said U.S. Pat. No. 4,021,326. The completed sensing element may then be installed in the appropriate housing in known manner.

As is apparent from FIGS. 1 and 2, the term "tubular" is used to denote the generally tubular characteristics of the element. The element will usually not have cylindrical walls and the term "tubular" refers to the elongated portion which in the embodiments of FIGS. 1 and 4 is gently tapered toward the closed end. It is apparent that this taper could be a steeper taper or that it could be nonexistent or even a negative taper; such elements being encompassed by the term "tubular" as used herein.

The sensor elements of the present invention when compared with those manufactured entirely from calcium oxide stabilized zirconium dioxide have the advantage of better electrical characteristics. These advantages are obtained with only relatively small additional cost since the governing electrical characteristics are derived from the material at the end of the heated sensor. The sensors of the present invention have the additional advantage that they are manufactured with relative ease. The manufacturing methods described hereinbefore in connection with the apparatus of FIGS. 5 and 6 are particularly advantageous because the manufacturing time and the number of manufacturing steps are substantially the same as those required for the manufacture of a closed end solid electrolytic tube made of a single material rather than the two materials of the tubular elements of the present invention.

A suitable glass with a coefficient of expansion of about $9 \cdot 10^{-6}$ has the following composition:
50% by weight BaO
5% by weight MgO
42% by weight $SiO_2$
3% by weight $Al_2O_3$ Preparation of an aqueous suspension of glass powder:

The glass mentioned above is premilled to a specific surface according to BET of $\geq 0.9 m^2/g$. This glass powder is mixed with 5% by weight kaolin and 5% by weight $BaCO_3$ and then, after adding the same part by weight of water, milled in a ball mill to a specific surface according to BET of 2 to 3 $m^2/g$. After milling an organic binding or adhesive agent is added such as 0.5 to 1% by weight polyvinylacohol related to the solid substance.

In addition to the method mentioned above there is the possibility of applying the layer 5 in FIG. 2 onto the end plate 4 in the form of a suspension of glass powder (as mentioned in the preceding paragraphe) in an organic binder. For that purpose the glass powder is mixed to form a paste with a screen printing oil of commercial size and printed on the end plate 4 by screen printing.

Example for the preparation of the annulus 5 in FIG. 3:

The aqueous suspension of the glass powder as described above is mixed with 2% by weight (related to the solid material) of a suspension of wax, then dried and powdered in mortar or a mill. The resulting powder is then axially pressed into the form of an annulus under a pressure of 500 to 1000 bar.

Conditions of the heat treatment for connecting the ceramic parts by glass:

Heating:
to 600° C.: gradient $\leq 200$ K/h
600° C. to end temperature: gradient 100 to 400 K/h
temperature 1200° to 1250° C.
halt: 1 hour
cooling: gradient 100 to 300 K/h
atmosphere: oxidizing The shaping of the separate ceramic parts is made by known methods:

Tubular element: quasi- isostatic pressure method with a pressure of 300 to 600 bar and forming of the outer form by grinding as described with reference to FIGS. 5 and 6.
Rounded element 7 of FIG. 4: isostatic pressure method with a pressure of 300 to 600 bar.
End plate 4 of FIGS. 2 and 3: axial pressure method with a pressure of 300 to 600 bar.
For all the cited pressing steps the ceramic material is granulated according to known methods, e.g. by spray drying, using 0.5 to 1% by weight of an emulsion of wax as pressing adjuvant or binder.

Suitable conditions for the preheating of the separate ceramic parts:

Heating:
to 600° C.: gradient $\leq 200$ K/h
600° C. to 950° C.: gradient $\geq 100$ K/h $\leq 300$ K/h
temperature: 950° C.
halt: 1 hour
cooling: gradient 400 K/h The conditions for sintering the ceramic depend on the composition and the degree of pulverization. The heating must be slow until the escape of the organic binder (about 600° C.). The sintering is made in an oxidizing atmosphere. For the examples described above the conditions for sintering are:

Heating:
to 600° C.: gradient $\leq 200$ K/h
600° C. to end temperature: gradient $\geq 50$ $\leq 300$ K/h
temperature: 1570° to 1630° C.
halt: 2 to 6 hours
cooling: gradient $\leq 400$ k/h Preferred regions of the ceramic composition:
CaO-stabilized: 10 to 18 mole % CaO
$Y_2O_3$- and/or $Yb_2O_3$-stabilized: 5 to 8 mole % $Y_2O_3$ and/or $Yb_2O_3$.

I claim:

1. A closed ended tubular solid electrolyte oxygen sensor element comprising a generally tubular portion having an integral closed end portion, said generally tubular portion consisting essentially of zirconium dioxide stabilized with calcium oxide, and said end portion consisting essentially of zirconium dioxide stabilized with at least one oxide selected from the group consisting of yttrium oxide and ytterbium oxide.

2. The element of claim 1 wherein said closed end portion is a thin plate.

3. The element of claim 1 wherein said closed end portion is a rounded portion.

4. The element of claim 1 wherein said elongated tubular portion consists essentially of zirconium dioxide stabilized with between about 8 and 25 mole percent calcium oxide, and wherein said end portion consists essentially of zirconium dioxide stabilized with between about 4 and 15 mole percent of at least one oxide selected from the group consisting of yttrium oxide and ytterbium oxide.

5. The element of claim 4 wherein said end portion consists essentially of zirconium dioxide stabilized with yttrium oxide.

6. The element of claim 4 wherein said end portion consists essentially of zirconium dioxide stabilized with ytterbium oxide.

7. The element of claim 4 containing between about 10 and 18 mole percent calcium oxide, and wherein said end portion contains between 5 and 8 mole percent of at least one oxide selected from the group consisting of yttrium oxide and ytterbium oxide.

8. The element of claim 7 wherein said end portion consists essentially of zirconium dioxide stabilized with yttrium oxide.

9. The element of claim 7 wherein said end portion consists essentially of zirconium dioxide stabilized with ytterbium oxide.

* * * * *